United States Patent
McElhinny et al.

(10) Patent No.: US 9,144,466 B2
(45) Date of Patent: Sep. 29, 2015

(54) APPARATUS FOR AUTOMATING THE COUNTING OF SHARPS USING RFID TAGS

(71) Applicant: Stryker Combo L.L.C., Bingham Farms, MI (US)

(72) Inventors: Michael T. McElhinny, Port Vue, PA (US); Steven J. Fleck, Pittsburgh, PA (US); Joshua J. Hill, Hubbard, OH (US)

(73) Assignee: STRYKER COMBO L.L.C., Bingham Farms, MI (US)

( * ) Notice: Subject to any disclaimer, the term of this patent is extended or adjusted under 35 U.S.C. 154(b) by 0 days.

(21) Appl. No.: 14/629,088

(22) Filed: Feb. 23, 2015

(65) Prior Publication Data

US 2015/0209111 A1    Jul. 30, 2015

Related U.S. Application Data

(62) Division of application No. 13/157,948, filed on Jun. 10, 2011, now Pat. No. 8,994,358.

(60) Provisional application No. 61/353,490, filed on Jun. 10, 2010.

(51) Int. Cl.
*G01N 27/00*      (2006.01)
*A61B 19/02*      (2006.01)

(52) U.S. Cl.
CPC .................. *A61B 19/0288* (2013.01)

(58) Field of Classification Search
USPC ........................................................ 324/71.1
See application file for complete search history.

(56) References Cited

U.S. PATENT DOCUMENTS

| | | | | |
|---|---|---|---|---|
| 2,888,136 A * | 5/1959 | La Borde | ....................... | 206/350 |
| 3,982,631 A * | 9/1976 | Kunik et al. | .................. | 206/380 |
| 4,013,109 A * | 3/1977 | Sandel | ........................ | 206/370 |
| 4,193,496 A * | 3/1980 | Barratt | ........................ | 206/380 |
| 4,259,633 A | 3/1981 | Rosenau | | |
| 4,373,629 A | 2/1983 | Ulin et al. | | |
| 4,918,375 A | 4/1990 | Malicki et al. | | |
| 5,024,326 A | 6/1991 | Sandel et al. | | |
| 5,063,370 A | 11/1991 | Smith | | |
| 5,193,678 A | 3/1993 | Janocik et al. | | |
| 5,508,681 A | 4/1996 | Nelson et al. | | |
| 5,868,709 A | 2/1999 | Champion et al. | | |
| 7,688,215 B2 | 3/2010 | Vokey et al. | | |
| 2008/0231452 A1 | 9/2008 | Levin | | |
| 2012/0311839 A1* | 12/2012 | Limaye | ....................... | 29/426.5 |

FOREIGN PATENT DOCUMENTS

WO         03028937 A1    10/2003

OTHER PUBLICATIONS

International Search Report; PCT/US2011/039906; Nov. 2011.
Written Opinion of the International Searching Authority, PCT/US2011/039906; Nov. 2011.

\* cited by examiner

*Primary Examiner* — Thomas F Valone
(74) *Attorney, Agent, or Firm* — Howard & Howard Attoneys PLLC

(57) ABSTRACT

In accordance with the teachings described herein, systems and methods are provided for counting sharps returned to a container. An example method of counting sharps returned to a container having at least two layers of penetrable conductive material includes periodically checking a plurality of circuits formed by the first and second layers of material to determine if each circuit is open or closed, and keeping a count of the number of closed circuits.

7 Claims, 16 Drawing Sheets

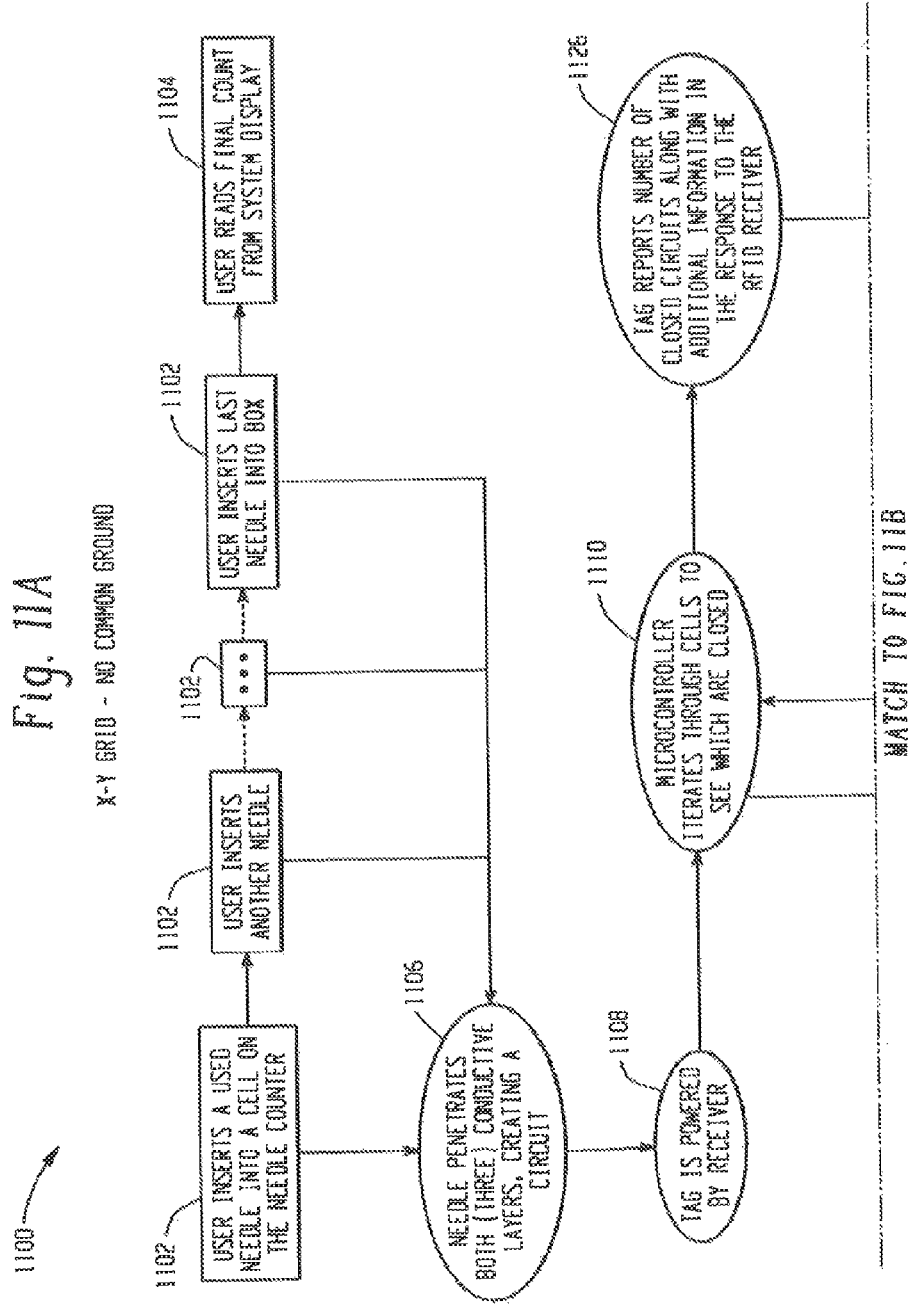

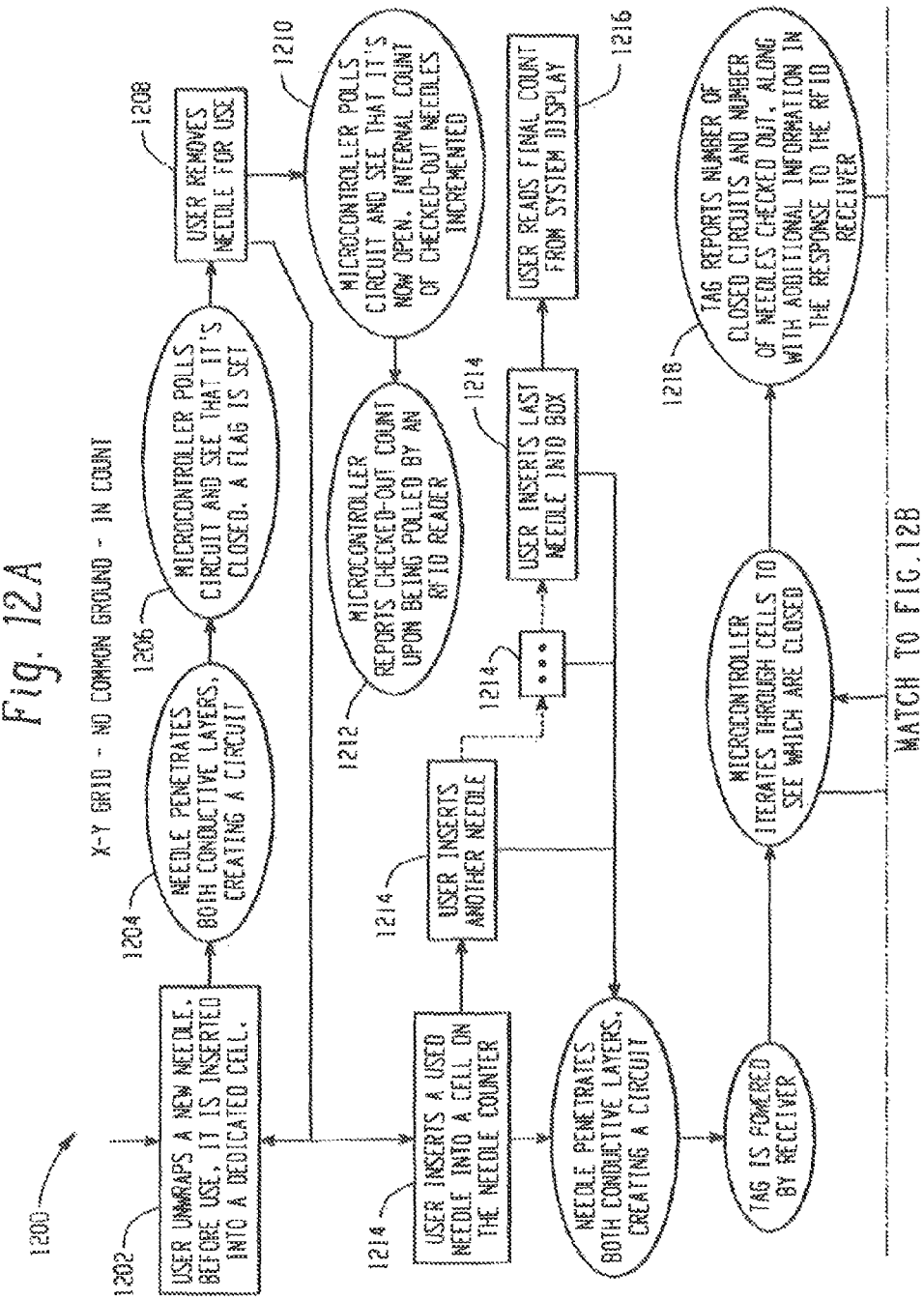

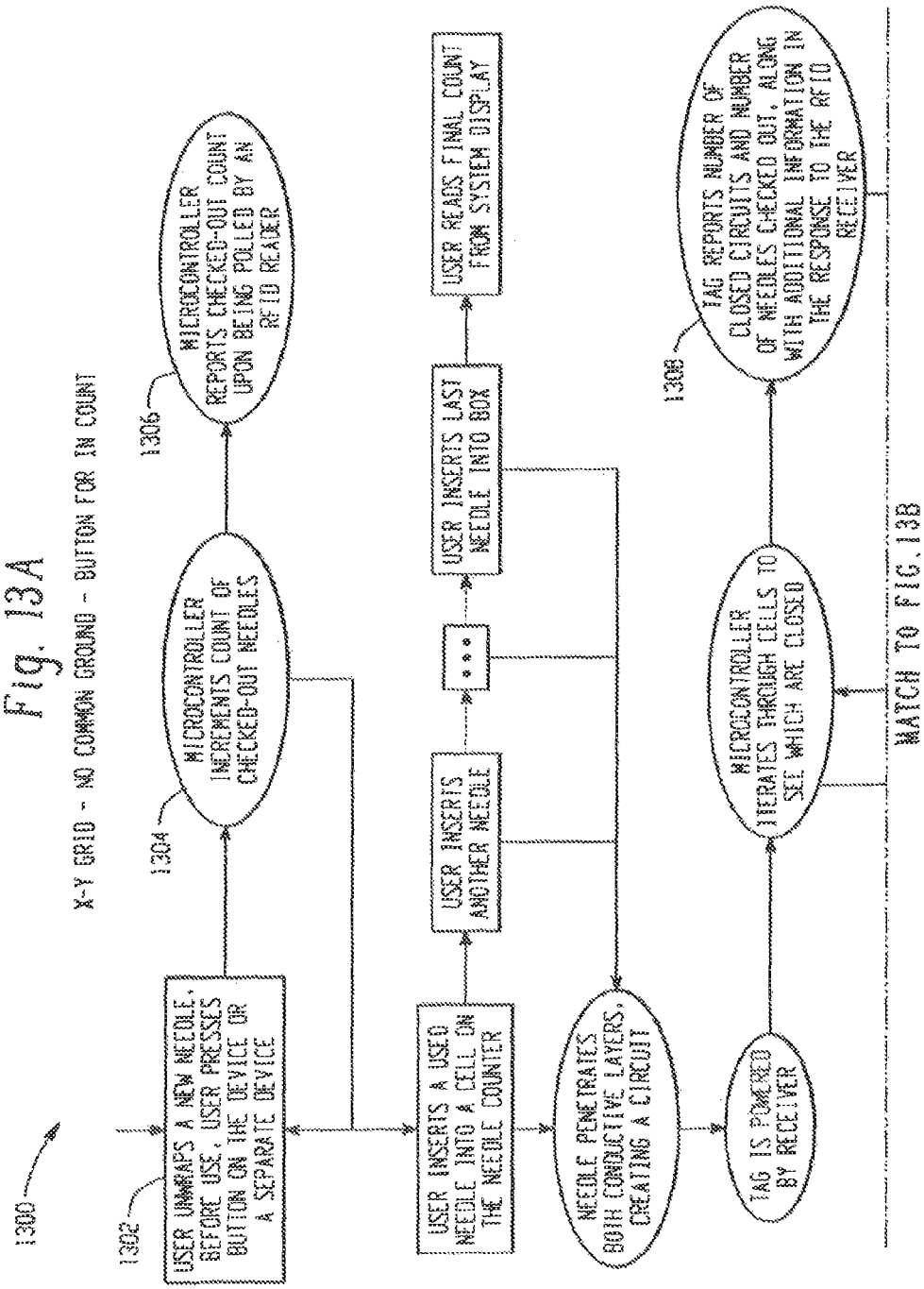

APPARATUS FOR AUTOMATING THE COUNTING OF SHARPS USING RFID TAGS

CROSS-REFERENCE TO RELATED APPLICATIONS

This application is a divisional of U.S. patent application Ser. No. 13/157,948, filed Jun. 10, 2011, and entitled "Method and Apparatus for Automating the Counting of Sharps Using RFID Tags," which claims priority to and benefit from U.S. Provisional Patent Application No. 61/353,490, filed on Jun. 10, 2010, and entitled "Method and Apparatus for Automating the Counting of Sharps Using RFID Tags," the entirety of each of which is incorporated herein by reference in their entirety.

BACKGROUND

The present disclosure is directed to methods and apparatus for the counting of needles, scalpel blades, and other sharps and, more particularly, to the application of radio frequency identification devices (RFID) used to automate such counts.

This disclosure addresses the issue of counting sharps in and around the operating room. Current technology automates the counting of some items in the operating room, such as surgical sponges, by affixing an RFID tag to the item. Objects such as needles and scalpel blades are not conducive to tagging because of their small size and because the smooth profile of the object is essential to the function of the object. Therefore, even if RFID tags were miniaturized, there would not be a suitable location on the exterior surface of a needle or scalpel blade for placement of a tag. The current state of needle counting technology consists of many variations of mechanical needle counting devices. These devices provide numbered spaces, slots, foam blocks, magnets, among others, usually all carried within a hard plastic clam-shell type of box that can be snapped shut after the box is filled with sharps. These devices vary primarily in size and needle capacity, but also differentiate through features such as magnetic areas where needles and blades may be placed to prevent falling out, fixtures for removing needles from syringes and blades from scalpels, safety hinges, etc.

We have polled various nursing staffs and have found almost unanimous interest in a solution that would automate the counting of needles, and/or validate the manual counts, and/or assist in entering these counts into the electronic medical record. A need exists for a product that can provide these various functions.

SUMMARY

A preferred embodiment of the present disclosure has a housing of a hard material, preferably plastic. One or more hinges are provided whereby the container can be opened, usually along a bisecting line, to reveal two "tray-like" halves with walls of some height, intended to contain sharps throughout a procedure. On the interior of one, or the other, or both halves of the container, there is a marked foam material. The side or sides of the container whose interior is covered with a foam material will continue to be used to facilitate needle/sharps counting in an identical manner to current products. In current products, this is accomplished by using a foam that is easily punctured by the sharps. The foam is of a sufficient thickness and possesses the proper material properties to hold the sharps in place after the sharps are inserted into the foam. The foam surface traditionally assists in counting by providing a printed grid pattern on the surface of the foam material. The user places one sharp per grid space, thereby making counting easier by providing visual cues that are easy to see.

In addition to providing this standard functionality, the present invention provides an "electronic count" of the needles and other sharps placed into this foam material with a printed grid pattern. To provide the electronic count, unlike the prior art devices which use a uniform piece of foam, the present invention uses layers of conductive and non-conductive foam (a multi-layer foam assembly). As the sharps are punctured through the multi-layer foam assembly, one or more circuits will be completed or the capacitance between the layers will be changed from a baseline capacitance measurement. The status of these various circuits or the change in capacitance values communicates the presence and/or quantity of sharps in the foam assembly, thus providing additional information to the user.

In one embodiment, a single layer of conductive foam forms the ground plane, and is commonly accessible to all sharps placed in the multi-layer foam assembly. The ground plane could be the top or bottom layer of the foam assembly. A second layer is comprised of conductive foam patches or grid elements, separated by non-conductive material, such as non-conductive foam, such that the single layer has some number of conductive areas, separated completely (electronically isolated) from all other conductive areas in the layer. Presumably the conductive areas collectively comprise the great majority of surface area compared to the nonconductive areas. A middle layer of nonconductive material, such as nonconductive foam, separates the two layers described above.

The single common ground plane foam layer has a lead, in the form of a wire or other conductive trace, connecting it to the ground pin of an analog or digital circuit component. Each conductive region of the second layer has a lead connecting it to the same circuit.

The multi-layer foam assembly, when constructed in the above manner, represents some number of open circuits connected to a circuit capable of sensing whether these circuits are open or closed. The act of piercing the multi-layer foam assembly will dramatically lower the resistance in the circuit, in essence closing the open circuit.

Other embodiments of the invention include, but are not limited to a multi-layered foam assembly with more than the three layers described here. Additional top and bottom layers may be desirable for protection of the foam, to facilitate printing, to add adhesive, etc. Adding more intermediate layers (both those containing a grid pattern of conductive areas, and those that constitute a single ground plane) provides for more opportunities for the sharp to close the electrical circuit. By staggering or offsetting multiple layers, one could provide more precise location information of the sharps. This could allow for multiple sharps accidentally placed in the same printed grid space to be individually recognized and therefore reduce the possibility for errors. The embodiment described above is referred to as an X to ground Y to ground type of sensing. Strips of foam positioned to define rows in one layer and columns in another layer, with or without a ground plane, may also be used.

In yet other embodiment, the grid formed by the upper and lower layers of conductive foam strips also forms a series of capacitors at the intersection points of the rows and columns. For example, a foam assembly may be constructed of 10 conductive foam strips in a top layer oriented in horizontal rows, and 5 conductive foam strips oriented in vertical columns, separated by a nonconductive layer. In this configuration, there would be 50 intersection points, creating 50 distinct capacitors. The capacitance of each intersection point could be monitored by a control unit such as a microcontroller; additionally this microcontroller may be supplemented by a specialized integrated circuit such as a capacitive sensing module (CSM) that is adapted for sensing a large number of capacitors in a grid formation. An example of such a CSM module is the Microchip mTouch TB3064.

In this embodiment, the capacitive sensing module would be connected to each of the X and Y rows and columns, and would be capable of addressing one row/column combination at a time by selecting the appropriate input/output channels and grounding the others. For each row/column combination, the capacitance of the intersection point is measured using one of several techniques. These techniques include, but are not limited to, the relaxation oscillator technique, charge time vs. voltage technique, or the voltage divider technique. The Microchip mTouch TBS 064 uses the relaxation oscillator technique. In this technique, the control unit or CSM contains an RC oscillator circuit which uses as its capacitance the capacitance of the row/column intersection. Thus the capacitance of the row/column intersection determines the oscillator's frequency which is monitored by the CSM. The CSM establishes a baseline capacitance value based on, among other factors, a predetermined or preprogrammed value or historical measured values. When a change in capacitance occurs between measurements, or when the measured capacitance differs by some threshold amount from the baseline value, the CSM signals the control unit. The CSM will measure every row/column combination in rapid succession. The control unit may apply some filtering to the data received from the CSM before determining that the change in capacitance does indeed represent a sharp puncturing the foam. For example, the control unit may apply some averaging to the data to filter out sporadic noise.

In yet other embodiments involving magnetic materials, pairs of electrical contacts may be provided, for example on a magnetic surface used to hold sharps safely inside the container. These electrical contacts would enable circuitry to determine which pairs of contacts are open and which pairs of contacts are shorted by the positioning of a scalpel blade or other sharp across a pair of contacts. Contacts could be positioned on a blade removal tool with the number of times a blade is inserted into the tool counted. Means can be provide to enable an "in count" to be taken. An "in count" is a count of the number of sharps available for use in the particular procedure. By comparing the "in count" to an "out count" (the number of sharps returned), an electronic verification that all sharps are accounted for can be provided. By providing RFID tags on sharps containers, data at the container about the container's contents can be transmitter for further use. The present invention includes various methods of using the different embodiments of disclosed sharps containers. The present invention automates the counting of needles, validates manual counts, and can assist in entering these counts into the electronic medical record. Those advantages and benefits, and others, will be apparent from the description container herein below.

BRIEF DESCRIPTION OF THE DRAWINGS

For the present invention to be easily understood and readily practiced, embodiments of the present invention will now be described, for purposes of illustration and not limitation, in conjunction with following figures.

FIGS. 11A and 11B show an example flow chart illustrating one method of using a sharps container constructed with an X-Y grid and no common ground plane.

FIGS. 12A and 12B show an example flow chart illustrating one method of using a sharps container constructed with an X-Y grid, no common ground plane, and which generates an "in count".

FIGS. 13A and 13B show an example flow chart illustrating one method of using a sharps container constructed with an X-Y grid, no common ground plane, and which generates an "in count" with a button or switch.

DETAILED DESCRIPTION

Figure 1:
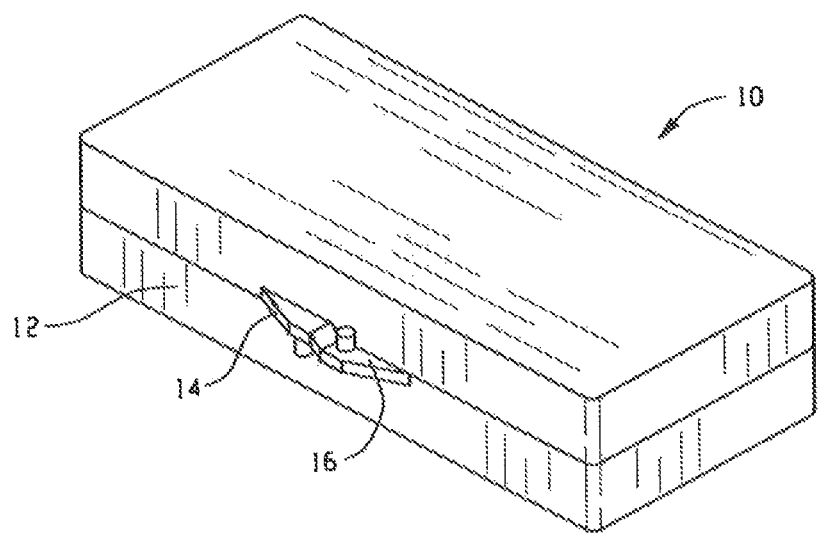
FIG. 1 illustrates a container.

Illustrated in FIG. 1 is a container 10 constructed according to the teachings of the present invention. The container 10 is constructed of a housing 12 of a hard material, preferably plastic. A latch comprised of an upper part 14 and a lower part 16 is provided. Those of ordinary skill in the art will recognize that the side of the housing 12 opposite the side carrying the latch, which is not visible in FIG. 1, carries one or more hinges which enable the container 10 to be opened as shown in FIG. 2.

Figure 2:
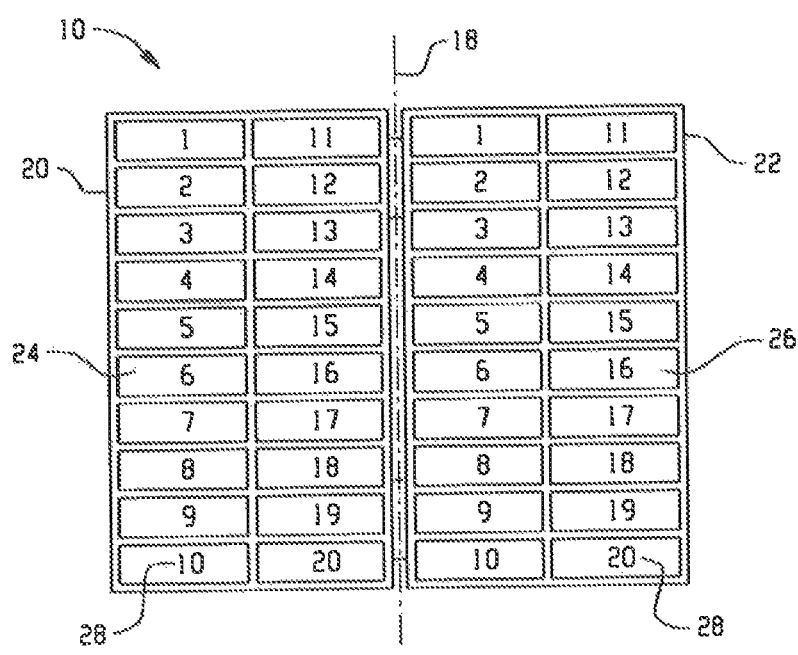
FIG. 2 illustrates the container of FIG. 1 in an opened condition.

The hinges are usually provided along a bisecting line 18 seen in FIG. 2. When the housing 12 is open as shown in FIG. 2, two "tray-like" halves 20, 22 with walls of some height are provided for the purpose of containing the sharps used throughout a procedure. The hinges may be of a type that can be separated and re-joined, allowing the user to place each half 20, 22 of the housing 12 in a different location. The hinges may be of a locking safety type that allow for the separation of the detachable hinges only when the container 10 is opened, and not when in the closed position.

Each half 20, 22 of the container 10 carries a specialized component comprised of, for example, a foam material 24, 26, respectively, shown in FIG. 2, or a magnetic material (not shown in FIG. 2). When magnetic material is present, the magnetic material is helpful as a "holding place" for needles and other metallic sharps during the procedure. In the prior art, this magnetic material is not used to facilitate any type of counting. However, as will be described below, in the present invention, this magnetic material may be modified to enable "out counting," i.e. when a sharp is no longer being used in the procedure and is returned to the sharps container.

In one embodiment, this disclosure focuses on the side(s) of the container 10 normally carrying a foam material. It should be noted that implementations of the present invention will, however, need to consider various features. For example, one embodiment of the invention may require circuitry on both sides of the container 10 connected by wires or flexible PCB material. That may conflict with the desire to separate the two halves of the container 10. Also, the effects of the magnetic material, if any, on an RFID transponder will need to be considered.

The sides of the container 20, 22 carrying the foam material 24, 26, respectively, are used to facilitate sharps counting in an identical manner to prior art products. In prior art products, the foam material is a single piece of foam having a printed grid pattern 28 on the surface of the foam material. Counting is accomplished by using a foam that is easily punctured by the sharps. The foam is of a sufficient thickness and density to hold the sharps in place after the sharps are inserted into the foam. The user places one sharp per grid space thereby making counting easier by providing visual cues that are easy to see.

In addition to providing that standard functionality, this invention provides an "electronic count" of the sharps placed into foam pieces 24, 26 carrying the printed grid pattern 28. To provide the electronic count, unlike the prior art devices which use a single layer of foam, the present invention uses layers of conductive and non-conductive foam (a multi-layer foam assembly). As the foam is punctured by insertion of sharps, a circuit is completed. The status of these various circuits communicates the presence and/or quantity of sharps in the foam, thus providing additional information to the user.

Figure 3A:
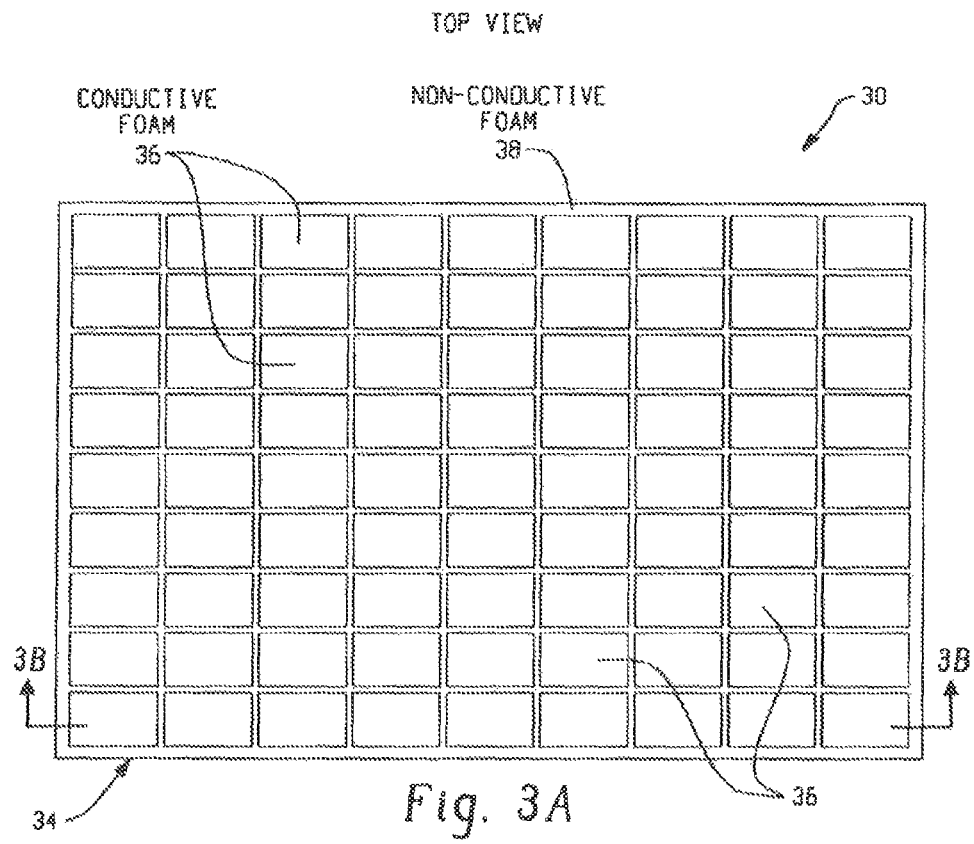
FIGS. 3A and 3B illustrate a multi-layer foam assemble implementing an isolated pad to ground type of sensing.
Figure 3B:
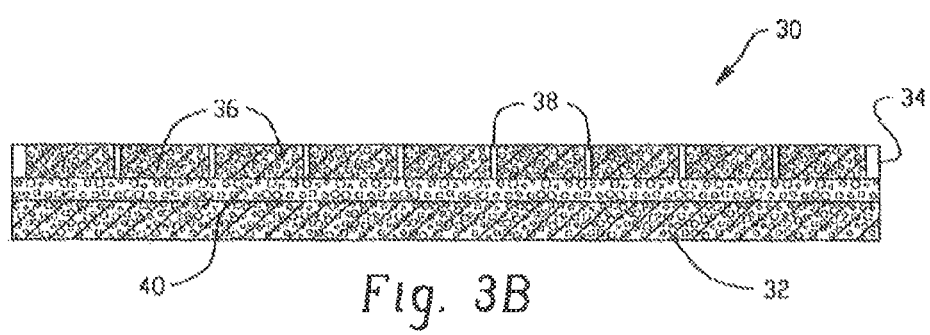

In one embodiment illustrated in FIGS. 3A and 3B, the multi-layer foam assembly 30 comprises a single layer of conductive foam 32 forming a ground plane that is commonly accessible to all sharps placed in the multi-layer foam assembly 30. The ground plane 32 could be the top or bottom layer of the foam assembly 30.

A second layer 34 is comprised of conductive foam patches or grid elements 36 separated by non-conductive material 38, such as non-conductive foam, such that the second layer 34 has some number of conductive areas separated completely (i.e., electronically isolated) from all other conductive areas in the layer. Presumably the conductive areas collectively comprise the great majority of surface area compared to the nonconductive areas. The conductive foam patches or grid elements 36 may or may not correspond to a grid pattern 28 printed on the top of the foam piece 24/26. A middle layer 40 of nonconductive material, such as nonconductive foam, separates the layers 32 and 34. In an alternative embodiment, one can imagine conductive inserts 36 placed into a layer of nonconductive material in a manner such that the conductive inserts do not extend to the bottom of the layer 34. In such an embodiment, the middle layer 40 could be eliminated.

Figure 4:
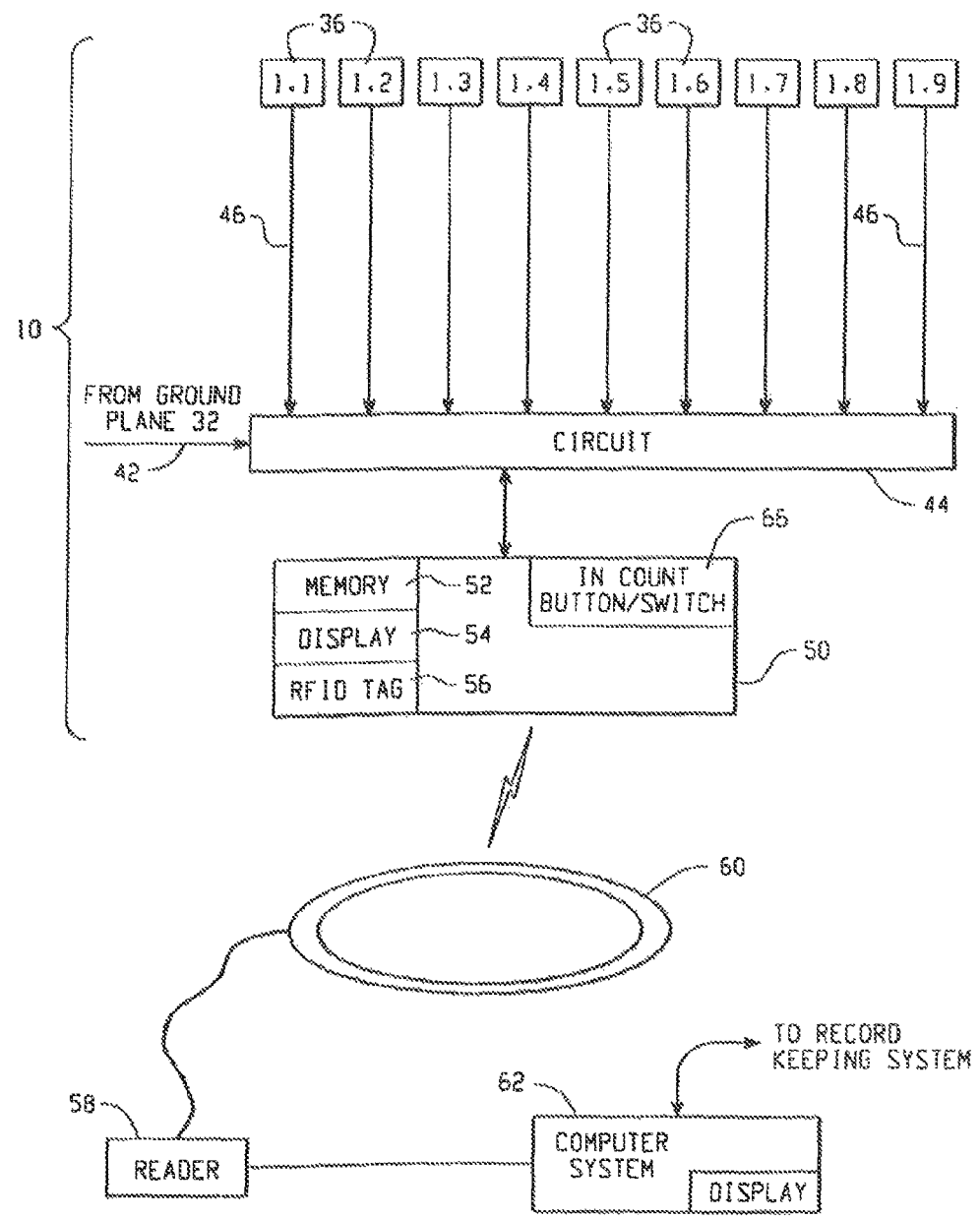
FIG. 4 is a block diagram of exemplary hardware which may be used to interrogate the multilayer foam assembly of FIGS. 3 A and 3B.

Turning to FIG. 4, the single common ground plane foam layer 32 has a lead, in the form of a wire, conductive trace, or the like 42, connecting the ground plane foam layer 32 to a ground pin of an analog or digital circuit 44. Shown in FIG. 4 is the first row of conductive regions labeled 1,1 through 1,9. Each conductive region 36 of the second layer 34 has a lead in the form of a wire, conductive trace, or the like 46 connecting the region 36 to the circuit 44. The multi-layer foam assembly 30, when constructed in this manner, represents a plurality of open circuits connected to the circuit 44. Piercing the multi-layer foam assembly 30 with a sharp, shorts the pierced conductive region 36 to the ground plane, dramatically lowering the resistance in that circuit and, in essence, closing the open circuit. The circuit 44 is capable of sensing whether each of the plurality of circuits between the conductive regions 36 and the ground plane 32 is open or closed. The number of circuits depends on the number of distinct conductive regions 36 that are constructed in the second foam layer 34. That will determine the number of sharps that are countable by the device.

The circuit 44 used to determine the open/closed status of each circuit between the conductive regions 36 and the ground plane 32 may be a common microcontroller with a sufficient number of I/O pins. This microcontroller may poll the circuits in response to a command from another circuit component, or may automatically do so based on a timer. The microcontroller may employ further logic to change the timing of this polling based on activity or on some other type of sensor input such as motion sensing. The microcontroller or another circuit component receiving the data representative of whether each circuit between the conductive regions 36 and the ground plane 32 is open or closed may log the data over some period, or may communicate the data to a secondary local or remote device 50 having a memory 52 for storage (such as in a digital count sheet or electronic medical record), a display 54, such as on a local LCD, perhaps on the container 10 itself, or more likely on a remote LCD screen.

Part of this secondary device 50 may be an RFID transponder or tag 56. The transponder 56 will likely be of the passive or Battery-Assisted Passive (BAP) type. The transponder 56 responds to commands from a nearby RFID reader 58 communicating through an antenna 60 to supply the transponder's 56 unique identification number (UID), as well as additional memory fields.

These additional memory fields may be programmed by the manufacturer and locked, and later used to identify the type or other characteristics of the item that carries the RFID tag. For example, the transponder 56 on the sharps container 10 could indicate to the interrogating reader 58 various attributes of the sharp counter such as:

The manufacturer of the sharps counter
Date of Manufacture/Lot number, etc.
Intended for which type(s) of sharps
Maximum capacity of sharps The memory field of the transponder 56 may have this information directly encoded in, for example, an ASCII character format, so that the interrogating reader 58 and any computer system 62 that is receiving the data does not need a look-up table to interpret it. Alternatively, each piece of information is represented by a code that is used to look up its meaning. Alternatively, a look-up table simply using ranges of UIDs may be used for the above purpose. This is generally too cumbersome to implement.

The RFID reader 58 polls the transponder 56 on the container 10, which commands the circuit 44 on-board the container 10 to query all of the circuits between the conductive regions 36 and the ground plane 32 and respond with the quantity of open/closed circuits. The RFID transponder 56 communicates this variable data, along with any other data it contained as discussed above. The RFID reader 58 is comprised of or is connected to a computer system 62, which is capable of interpreting both the static and variable data fields passed to it from the RFID transponder 56. The RFID reader 58 and computer system 62 could serve as the control/display unit responsible for interpreting, processing, storing, and communicating the data externally to a record keeping system, and/or displaying the information on a screen. It should be noted that because the RFID reader 58 and computer system 62 always associate the static and variable data with a UID, and would have the ability to properly associate multiple data sets with their corresponding UIDs, a single reader 58 could interrogate any number of RFID tagged sharps containers and be able to record/report/display data about each individual container, even when read by the same reader simultaneously.

For example, two different containers could be used, each with a different capacity and each intended for a different type of needle. A display connected to the RFID reader/computer could display the following:

CONTAINER #1: Needle Type A: 5 of 20 needles present
CONTAINER #2: Needle Type B: 3 of 10 needles present It is envisioned that the RFID reader/antenna would be a multi-purpose reader/antenna, such as the reader/antenna available from ClearCount Medical Solutions, Inc. of Pittsburgh Pa. Such a reader is intended for scanning sponges, towels, and other items tagged with RFID tags. The reader 58 may not be permanently mounted within reading distance of the RFID tagged sharps container, but instead the reader could be brought nearby when a count is desired. Alternatively, the RFID reader 58 could be of a tunnel-style or bucket-style, such as ClearCount's receptacle reader on its SmartSponge System. In this scenario, the sharps container could be placed in the receptacle when a count is wanted, such as at the very end of a procedure.

As an alternative to the device 44 polling the circuits between the conductive regions 36 and the ground plane 32 when instructed to by the RFID transponder 56, the polling could be done periodically by circuit 44 and the results saved in memory 52. Then when the reader 58 polls the transponder 56, the transponder 56 transfers the data from the memory 52 to the reader 58.

As an alternative to periodic querying of the RFID tagged sharps container 10, a more permanently positioned dedicated base station (not shown) could be employed. A base station would be in communication with the sharps counter 10 through the transponder 56 or through physical connections. The use of a dedicated base station using physical connections could have the further advantage of allowing for some portion of the circuitry needed on the sharps container to be placed on a reusable device, allowing the disposable sharps container to be made less complex and expensive.

The microprocessor 44 and secondary device 50 on the container 10 may be powered by one or more of the following means:

On-board battery, such as a small, light, and inexpensive cell that provides sufficient power for a single surgical procedure, and is intended to be disposed along with the sharps container at the end of the procedure.

If an RFID transponder or similar circuit is employed on the container, this device may 'harvest' ambient energy from an interrogating reader. This is commonly done with RFID transponders and is in fact how passive transponders function. It is conceivable that enough of this power is diverted to temporarily power the microcontroller 44 and secondary device 50 while the reader is in proximity.

A base station containing a power supply of any known type, with physical contact connectors, can provide power to the microprocessor 44 and secondary device 50 on the container 10. It is presumed that this would be a reusable piece of hardware.

A capacitor is used on-board the container and is either pre-charged or is charged via one of the two means described above, and allows for continuity of power for some time after the ambient energy or base station power source is removed.

It is possible to envision a multi-layered foam assembly with more than the three layers described here. Additional top and bottom layers may be desirable for protection of the foam, to facilitate printing, to add adhesive, etc. Adding more intermediate layers (both those containing a grid pattern of conductive areas, and those that constitute a single ground plane) provides for more opportunities for the sharp to close the electrical circuit. By staggering or offsetting multiple layers, one could provide more precise location information of the sharps. This could allow for multiple sharps accidentally placed in the same printed grid space to be individually recognized and therefore reduce the possibility for errors.

For example, if the printed grid size is 1 cm×1 cm, staggering or offsetting of multiple layers results in an effective electrical grid size of 0.25 cm×0.25 cm. That could reduce errors significantly. Other variations of the present invention involve the substitution of other materials for those described herein, the use of additional non-functional layers for spacing, adhesion, etc. among others.

Figures 5A, 5B:
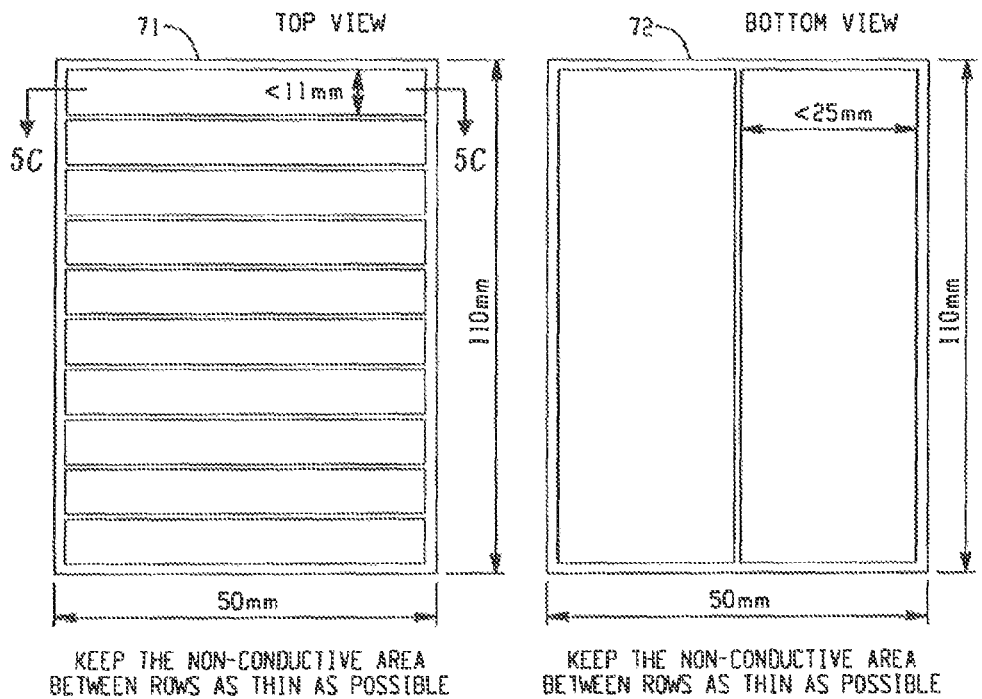
FIGS. 5A, 5B, and 5C illustrate a multi-layer foam assemble implementing an X-Y type of sensing.
Figure 5C:
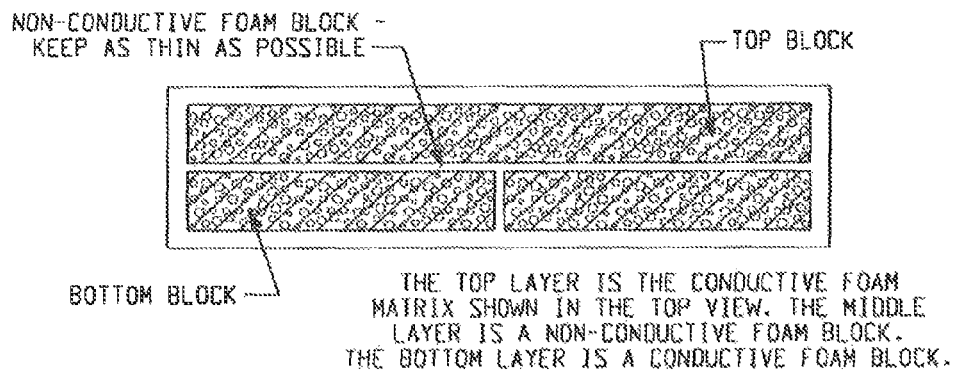
Figure 6:
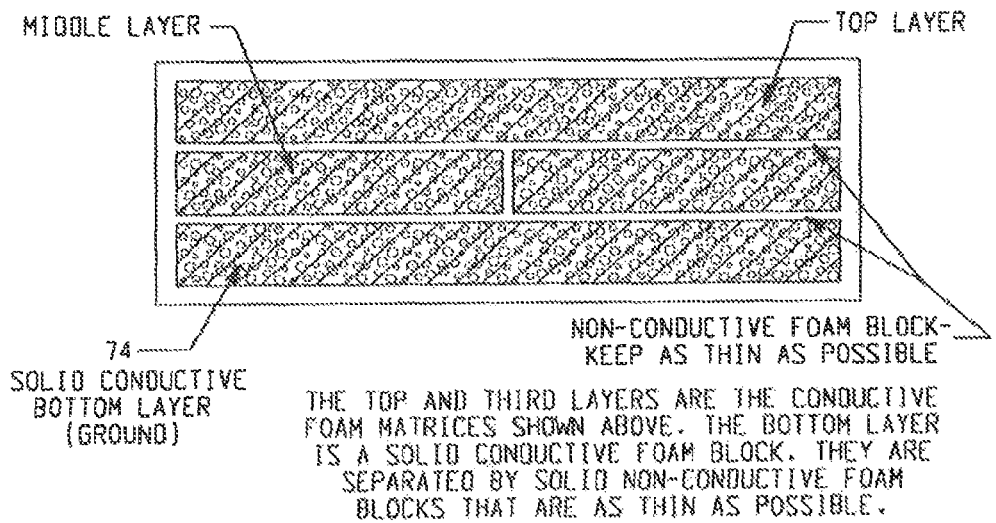
FIG. 6 a variation of the multi-layer foam assembly shown in FIGS. 5 A, 5B, and 5C modified to add a ground layer to implement an X to ground Y to ground type of sensing.

Variations of the multi-layer foam assembly are contemplated. One variation shown in FIGS. 5 A, 5B, and 5C provides a first grid pattern 71 of conductive foam and a second grid pattern 72 of conductive foam. Although each of the grid patterns alone does not provide unique grid locations, when stacked as shown in FIG. 5C, the grid patterns 71, 72 together provide a series of unique grid locations for a sharp placed through them by means of providing a unique combination of X and Y coordinates. Each conductive foam 'column' and 'row' is treated as an input to a circuit 44 of the type shown in FIG. 4, and additional logic is provided to calculate the X and Y coordinates (i.e., the position or location) of sharps present based on the collective status of the column and row circuits. Depending on the capabilities and available pins on the circuit used to determine if a circuit is open or closed, a ground plane 74 may be necessary as shown in FIG. 6. The multi-layer foam assembly of FIGS. 5A, 5B, and 5C is used to implement an X-Y type of sensing while the multi-layer foam assembly of FIG. 6 is used to implement an X to ground Y to ground type of sensing. These variations may be polled by the circuit shown in FIG. 4 with logic added to calculate position information.

Figure 7:
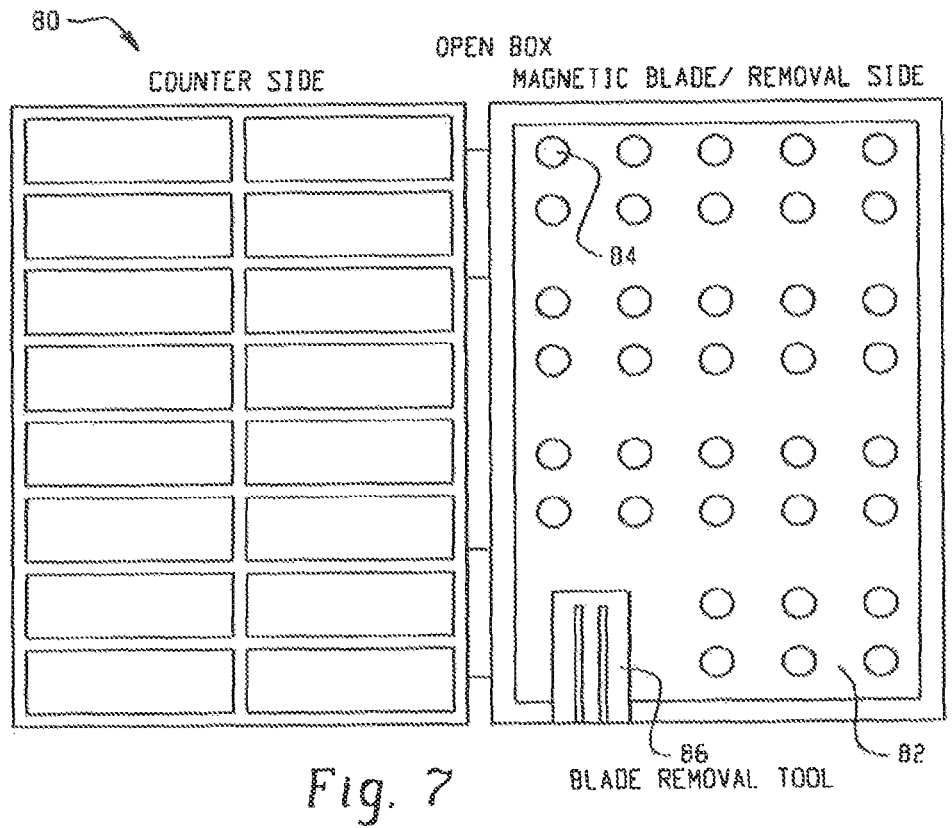
FIG. 7 illustrates a sharps container having on the left side a multi-layer foam assembly and on the right said a magnetic material having a plurality of electrical contacts.

FIG. 7 illustrates another type of sharps container 80. The sharps container 80 has, on the left side, a multi-layer foam assembly of the type previously described. On the right side of the container 80, a magnetic material 82 is provided. The magnetic material 82 may be provided with a plurality of electrical contacts 84. When a used scalpel blade is positioned between a pair of contacts 84, a circuit is closed between those contacts indicating that a scalpel blade has been stored in the container 80. Circuitry of the type shown in FIG. 4 may be used to periodically poll pairs of contacts 84 to determine which are open and which have been closed by the positioning of a blade therebetween. The magnetic material will hold the used blade on the contacts 84. A switch 66 (see FIG. 4) may be used to manually "in count" the number of scalpel blades used for the procedure. A blade removal tool 86 may also be provided as is known in the art.

Figure 8:
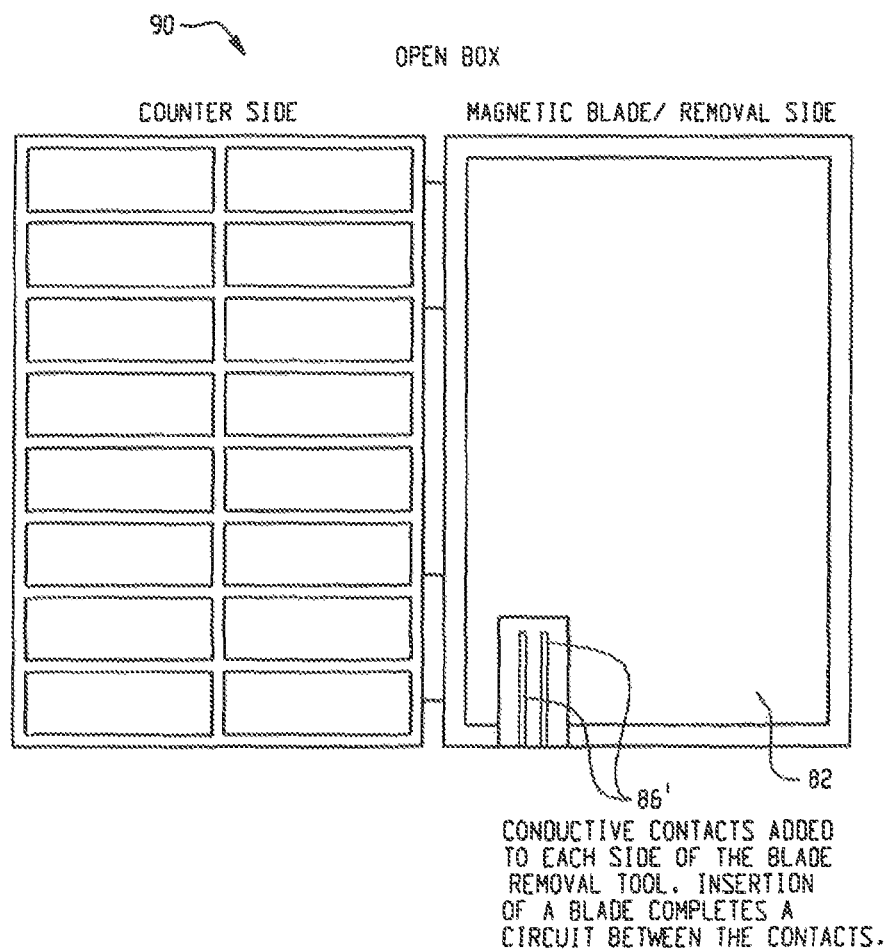
FIG. 8 illustrates a sharps container having on the left side a multi-layer foam assembly and on the right said a magnetic material having a blade removal tool having a pair of electrical contacts.

FIG. 8 illustrates another type of sharps container 90. Sharps container 90 is similar to sharps container 80 in that sharps container 90 has, on the left side, a multi-layer foam assembly of the type previously described and, on the right side, a magnetic material 82. Sharps container 90 does not have the plurality of contacts 84. Rather, a blade removal tool 86' is equipped with a pair of electrical contacts which enable a circuit to be closed each time a scalpel blade is inserted into the removal tool. In that manner, a count of the returned blades (referred to as an "out count") can be maintained. A switch 66 (see FIG. 4) may be used to manually "in count" the number of scalpel blades used for the procedure. In either the embodiment shown in FIG. 7 or the embodiment shown in FIG. 8, comparing the "in count" with the "out count" provides an electronic verification that all blades have been delivered to the sharps container 80, 90.

Figure 9:
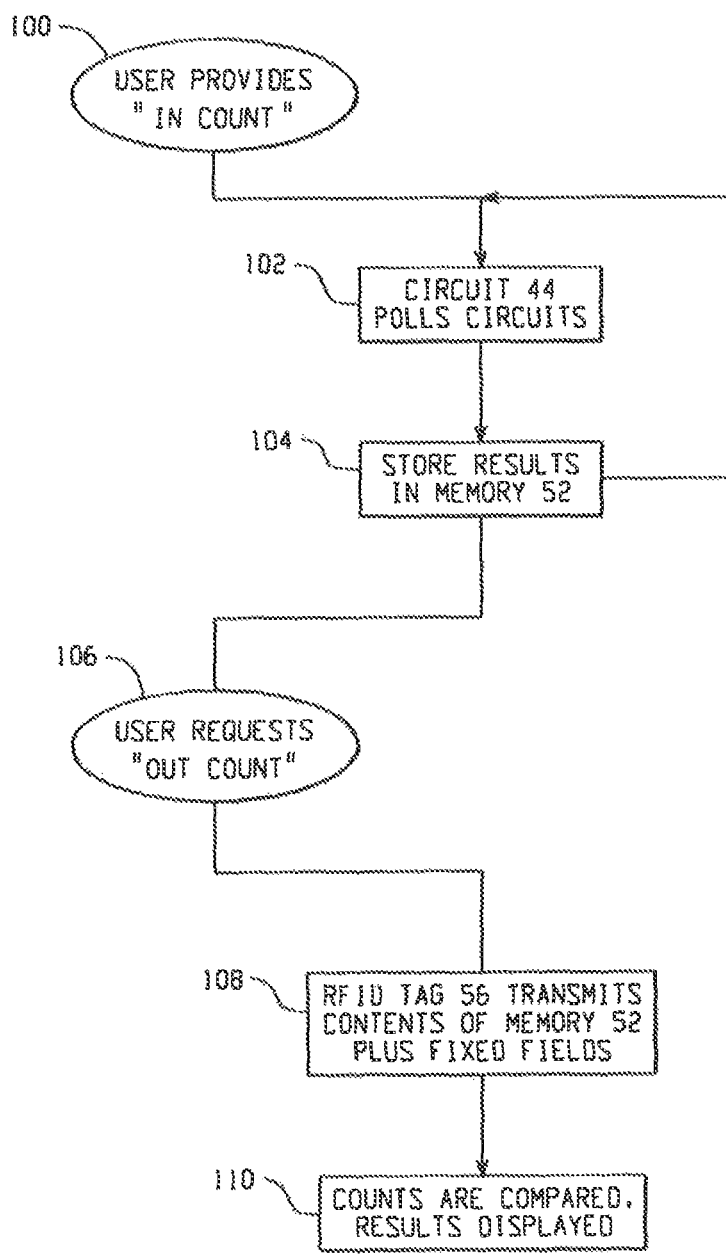
FIG. 9 is a flow chart illustrating the steps performed by the user/operator and the hardware shown in FIG. 4.

FIG. 9 illustrates a flow chart of the steps performed by a user/operator and the hardware shown in FIG. 4. In FIG. 9, and the other figures illustrating methods, rectangles represent user actions while ovals represent hardware actions. In FIG. 9, the process may begin with the optional step 100 of the user entering an "in count." Although not required, an "in count" enables an electronic verification that all sharps are accounted for. At step 102 the circuit 44 polls all of the circuits to which it is attached to determine which are open, which are closed and, depending on the configuration of the sharps container, the location of the circuit. The polling may be initiated by the user or a timer. Polling is accomplished in a number of ways:

- In the embodiment of FIGS. 3A and 3B, the circuit 44 determines for each conductive element 36 whether a sharp has penetrated the conductive element and penetrated the ground plane 32.
- In the embodiment of FIGS. 5A, 5B, and 5C, the circuit 44 determines if a sharp has penetrated both a row and a column of conductive material, and if so, the row number and column number.
- In the embodiment of FIG. 7, the circuit 44 determines which pairs of electrical contacts are open and which are shorted.
- In the embodiment of FIG. 8, the circuit 44 keeps track of how many times a blade has been inserted in the blade removal device 86'.

After the polling is completed, the results are stored in memory 52 at step 104.

At any time, the user may request a count of the returned sharps as shown at step 106. In the embodiment of FIG. 4, the reader 58 and antenna 60 are used to send the request to transponder 56. In other hardware configurations, the container may be brought into proximity to the antenna 60. When the antenna 60 is brought into rage of the transponder 56, the transponder transmits its unique ID, any information in fixed fields as discussed above, and the results of the polling taken from memory 52 as shown at 108. Finally, the results of the polling, which represents a count of the returned sharps, may be compared to the "in count" to verify that all sharps are accounted for or to indicate that one or more sharps are not accounted for as shown at step 110.

Figure 10:
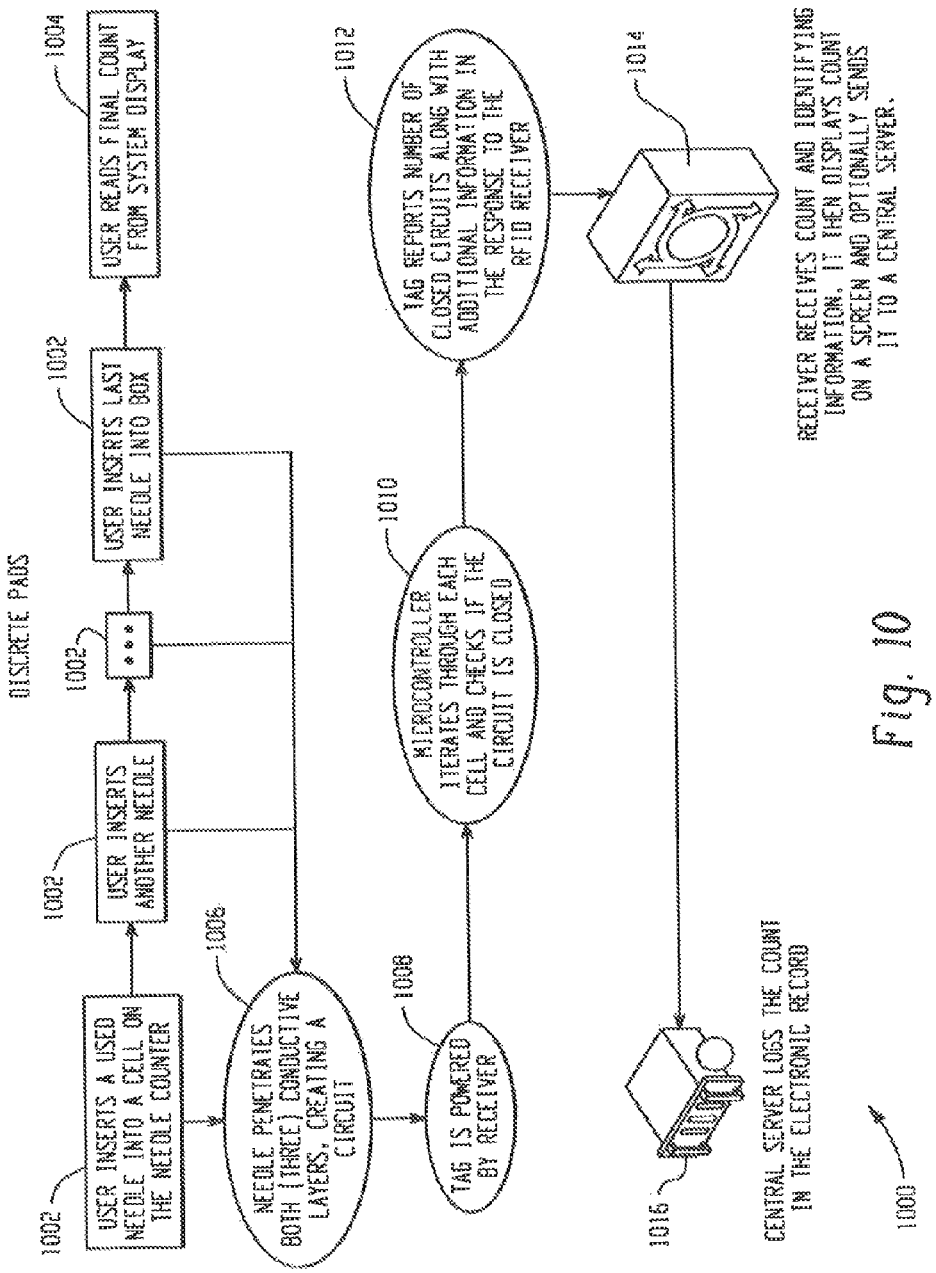
FIG. 10 shows an example flow chart illustrating one method of using a sharps container constructed with discrete conductive pads.

More detailed explanations of various methods of operation are illustrated in FIGS. 10-15. FIG. 10 shows at 1000 an example flow chart illustrating one method of using a sharps container constructed with discrete conductive pads. A microcontroller iterates through cells on a needle counter included in the sharps container, and generates information related to the number of needles inserted onto the needle counter based on the number of closed circuits formed by the inserted needles penetrating conductive layers with discrete conductive pads.

At 1002, a user inserts a number of needles into cells on the needle counter which has multiple conductive layers (e.g., two or three layers). At least one of the conductive layers has the discrete conductive pads. The needles penetrate both or three layers and close a certain number of circuits in the cells at 1006. After an RFID transponder or tag is powered up by an RFID receiver at 1008, the microcontroller iterates through each cell, and generates information related to the number of the inserted needles based on the number of closed circuits that are detected at 1010. Then the microcontroller provides, through the RFID transponder or tag, information related to the number of closed circuits along with additional information to the RFID receiver upon request at 1012. The RFID receiver identifies the received information and displays a final count of the needles inserted into the cells on the needle counter on a system display at 1014. The user can read the final count of the inserted needles on the system display at 1004. Optionally, the RFID receiver may transmit the received information to a central server which logs the final count in an electronic record at 1016.

Figure 11B:
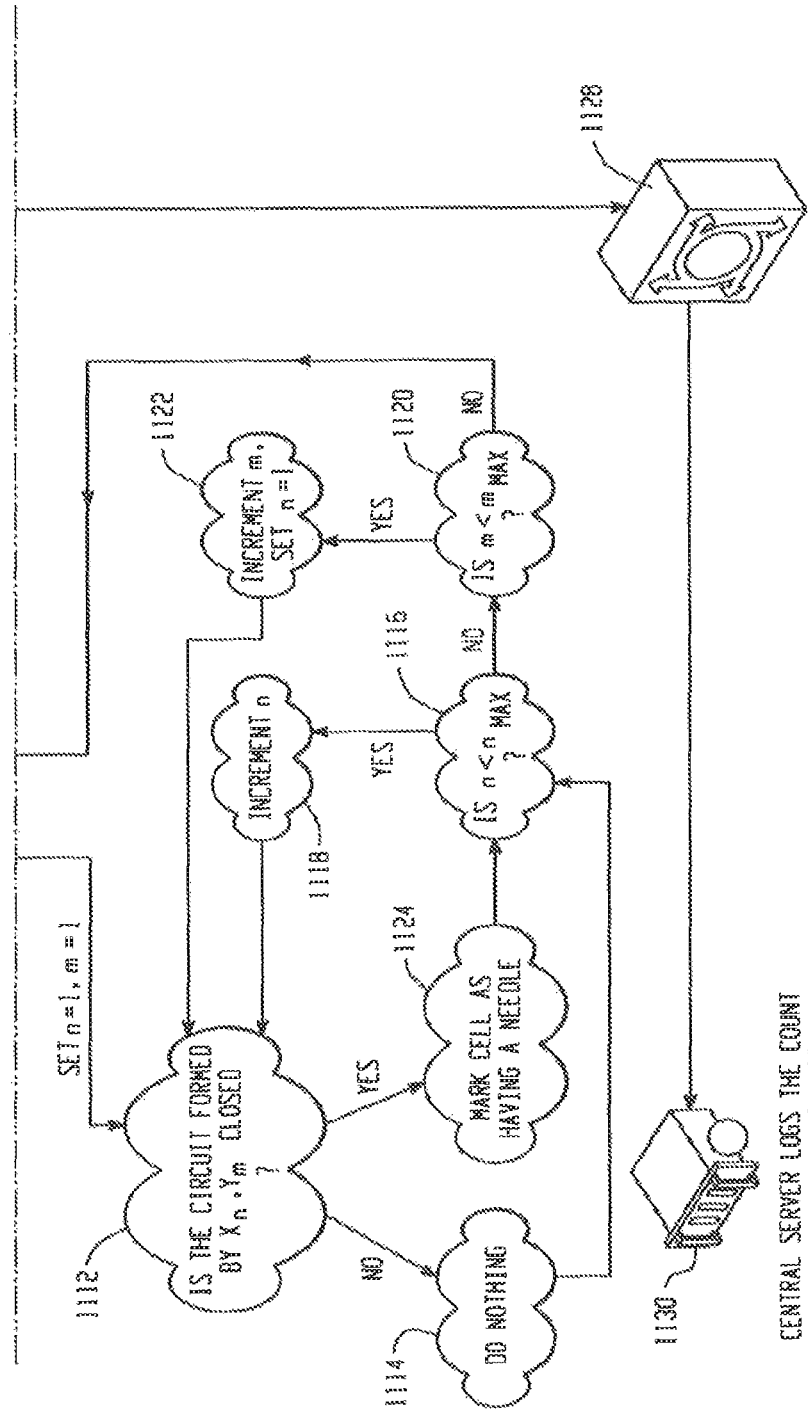

FIGS. 11A and 11B show at 1100 an example flow chart illustrating one method of using a sharps container constructed with an X-Y grid and no common ground plane. Based on stacked grid patterns, a microcontroller iterates through cells on a needle counter included in the sharps container, and generates information related to the number of needles inserted onto the needle counter based on the number of closed circuits detected.

Specifically, at 1102, a user inserts a number of needles into cells on the needle counter which includes multiple conductive layers (e.g., two or three layers). Two or more of the conductive layers include different grid patterns which are stacked together to provide a series of unique grid locations for an inserted needle using a unique combination of coordinates (e.g., X and Y coordinates). The needles penetrate both or three layers and close a certain number of circuits in the cells at 1106. After an RFID transponder or tag is powered up by an RFID receiver at 1108, the microcontroller iterates through cells to count the closed circuits at 1110. The microcontroller starts with a first cell formed by the stacked grid patterns, e.g., a cell at the crossing of a first "column" (n=1) and a first "row" (m=1) of the stacked grid patterns, and then proceed to check all other cells.

For a particular cell, the microcontroller determines whether a circuit is closed at 1112. If no closed circuit is detected, the particular cell is skipped at 1114. On the other hand, if a closed circuit is detected at the particular cell, the microcontroller marks, at 1124, the particular cell as having a needle. Then, a next cell is chosen to be checked until all cells have been visited by the microcontroller.

To choose a next cell, the microcontroller determines, at 1116, whether the particular cell is at the last column of the stacked grid patterns, e.g., whether n<nmax. If the particular cell is not at the last column, the next cell is chosen at the crossing of a next column (e.g., n is incremented) and the same row of the particular cell, at 1118. If the particular cell is at last column, then the microcontroller determines, at 1120, whether the particular cell is at the last row of the stacked grid patterns, e.g., whether m<mmax. If the particular cell is at the last row, it means all cells have been checked and the number of detected closed circuits is returned for reporting. If the particular cell is not at the last row, the next cell is chosen at the crossing of a next row (e.g., m is incremented) and the first column of the stacked grid patterns (e.g., n is set to be 1), at 1122.

Then the microcontroller provides, through the RFID transponder or tag, information related to the number of closed circuits along with additional information to the RFID receiver upon request at 1126. The RFID receiver identifies the received information and displays a final count of the needles inserted into the cells on the needle counter on a system display at 1128. The user can read the final count of the inserted needles on the system display at 1104. Optionally, the RFID receiver may transmit the received information to a central server which logs the final count in an electronic record at 1130.

Figure 12B:
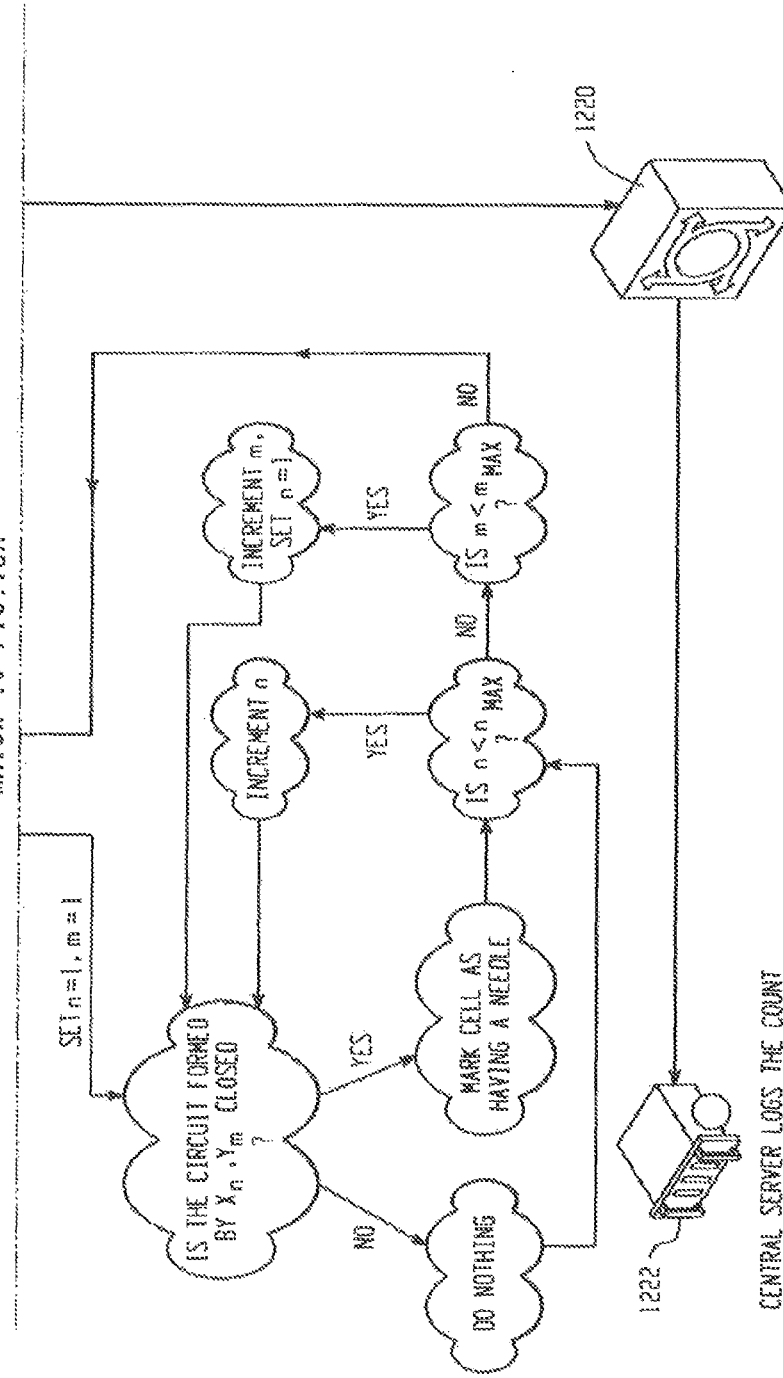

FIGS. 12A and 12B show at 1200 an example flow chart illustrating one method of using a sharps container constructed with an X-Y grid, no common ground plane, and which generates an "in count." A microcontroller polls dedicated cells to count the number of new needles that are checked out for use to establish the "in count" of the new needles. Then, based on stacked grid patterns, the microcontroller iterates through cells to count the number of needles that are returned after use to the sharps container for comparison with the "in count."

A user unwraps a number of new needles, and inserts the new needles into dedicated cells on the needle counter before use at 1202. The needle counter includes the stacked grid patterns. The needles penetrate both or three layers and close a certain number of circuits in the dedicated cells at 1204. The microcontroller sets a flag for each closed circuit formed by an inserted needle at 1206. After the user checks out a certain number of new needles for use at 1208, the microcontroller counts the number of open circuits resulted from the checked-out needles at 1210. Then the microcontroller provides reports of the number of the checked-out needles to an RFID receiver upon request at 1212.

At 1214, the user inserts a certain number of checked-out needles after use into cells on the needle counter. The microcontroller counts the number of the used needles based on the number of closed circuits that are detected similar to what is described for FIG. 11. Then the microcontroller provides, through an RFID transponder or tag on the sharps container, information related to the number of the detected closed circuits, the "in count," and additional information to the RFID receiver upon request at 1218. The RFID receiver identifies the received information and displays a final count of the needles returned after use and the "in count" for comparison on a system display at 1220. The user can read the final count of the needles returned after use and the "in count" on the system display at 1216. Optionally, the RFID receiver transmits the received information to a central server for recording at 1222.

Figure 13B:
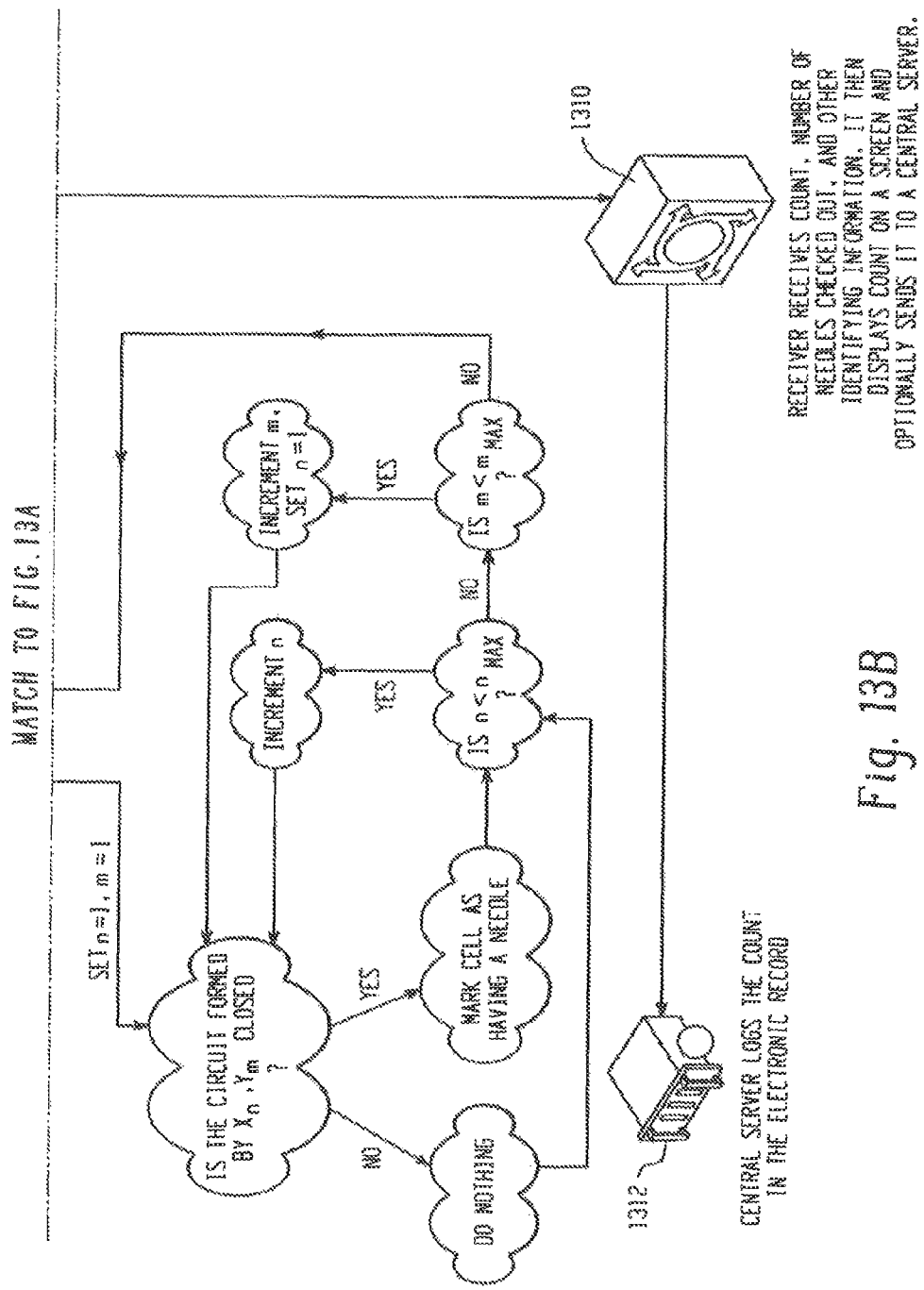

FIGS. 13A and 13B show at 1300 an example flow chart illustrating one method of using a sharps container constructed with an X-Y grid, no common ground plane, and which generates an "in count" with a button or switch. A microcontroller counts the number of new needles that are checked out for use to establish the "in count" of the new needles based on a user's manual input using the button or switch. Then, based on the stacked grid patterns, the microcontroller iterates through cells to count the number of the needles that are returned after use to the sharps container for comparison with the "in count."

A user unwraps a number of new needles, and presses a button or switch once for each needle to be checked out for use at 1302. The microcontroller counts the number of checked-out needles based on the user's manual input through the button or switch to establish the "in count" of the new needles, at 1304. Then, at 1306, the microcontroller provides reports of the number of checked-out needles to an RFID receiver upon request.

The microcontroller counts the number of the needles that are returned after use based on the number of closed circuits that are detected similar to what are described for FIGS. 11A and 11B and FIGS. 12A and 12B. Then, the microcontroller provides, through an RFID transponder or tag on the sharps container, information related to the number of the detected closed circuits, the "in count," and additional information to the RFID receiver upon request at 1308. The RFID receiver identifies the received information and displays a final count of the needles returned after use and the "in count" for comparison on a system display at 1310. Optionally, the RFID receiver may transmit the received information to a central server for recording at 1312.

Figure 14:
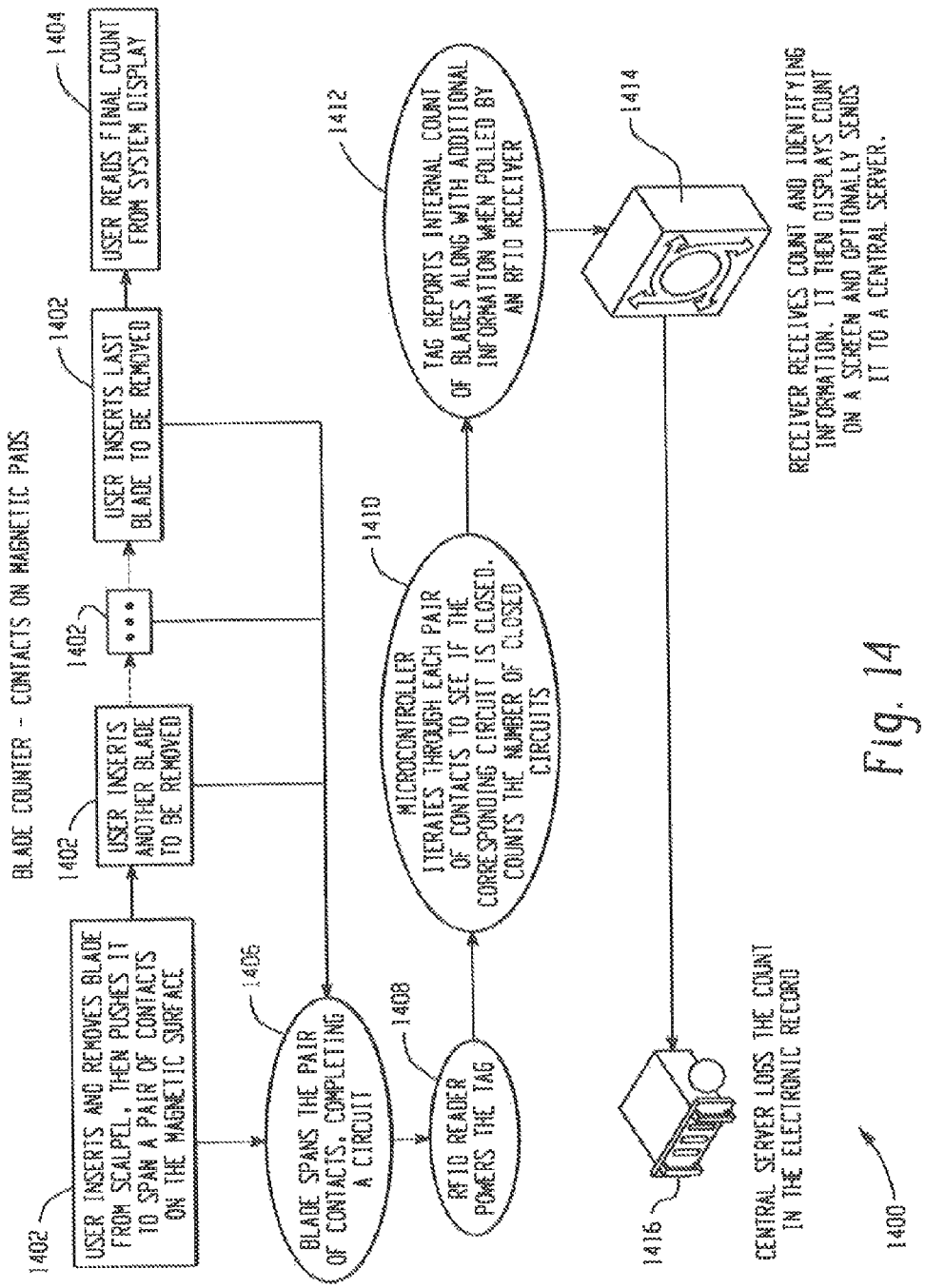
FIG. 14 shows an example flow chart illustrating one method of using a sharps container having contacts on magnetic pads.

FIG. 14 shows at 1400 an example flow chart illustrating one method of using a sharps container having contacts on magnetic pads. A microcontroller iterates through pairs of contacts on a magnetic surface included in the sharps container, and generates information related to the number of blades inserted into the sharps container based on the number of closed circuits formed by the inserted blades spanning the pairs of contacts.

At 1402, a user inserts a number of blades removed from scalpels onto the pairs of contacts on the magnetic surface in the sharps container at 1402. Each of the blades spans a pair of contacts, and thus closes a circuit at 1406. After an RFID transponder or tag is powered up by an RFID receiver at 1408, the microcontroller iterates through the pairs of contacts, and generates information related to the number of the inserted blades based on the number of closed circuits that are detected at 1410. Then the microcontroller provides, through the RFID transponder or tag, information related to the number of closed circuits along with additional information to the RFID receiver upon request at 1412. The RFID receiver identifies the received information and displays a final count of the inserted blades on a system display at 1414. The user can read the final count of the inserted blades on the system display at 1404. Optionally, the RFID receiver may transmit the received information to a central server which logs the final count in an electronic record at 1416.

Figure 15:
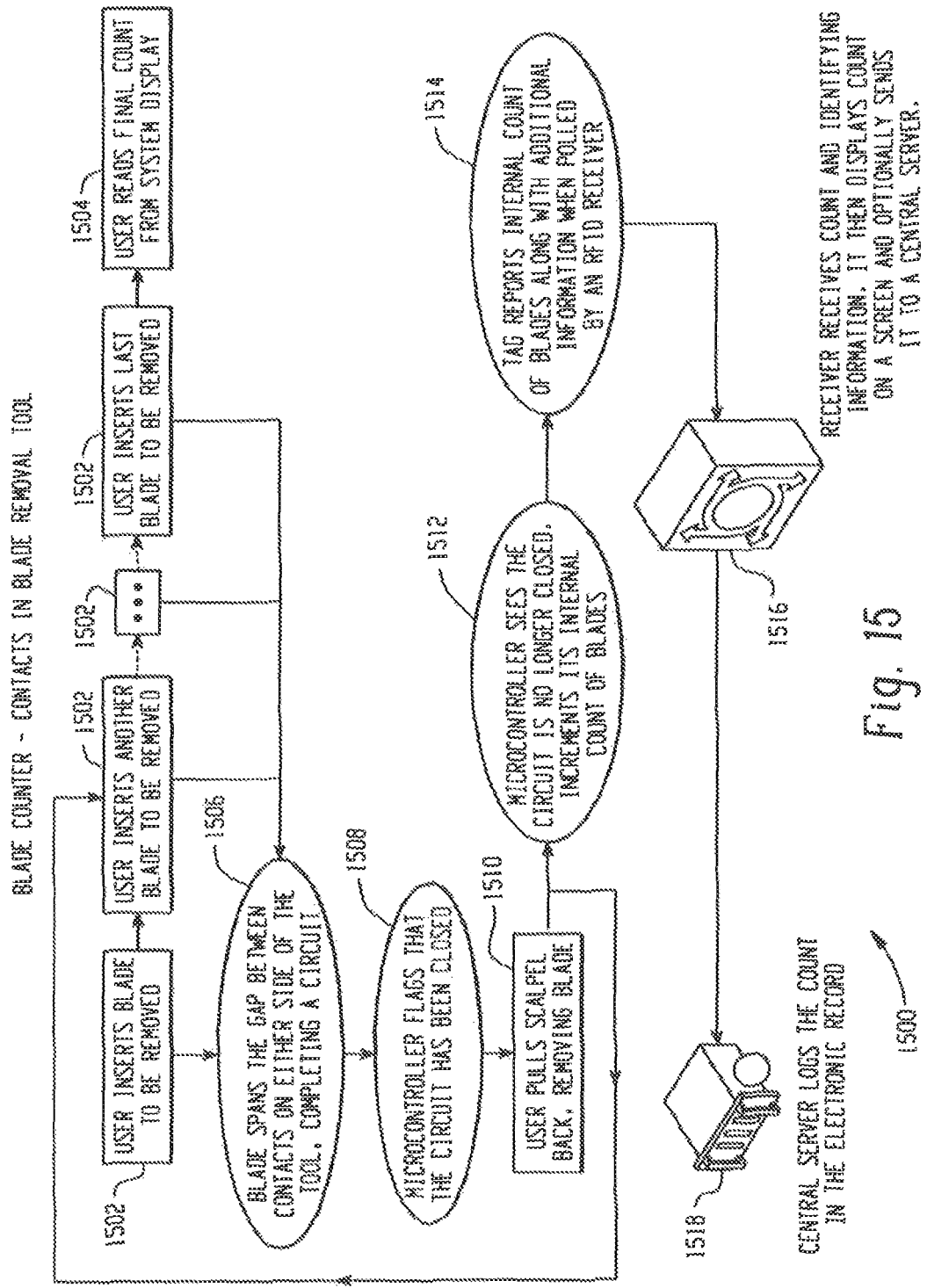
FIG. 15 shows an example flow chart illustrating one method of using a sharps container having contacts carried by a blade removal tool.

FIG. 15 shows at 1500 an example flow chart illustrating one method of using a sharps container having contacts carried by a blade removal tool. A microcontroller counts the number of blades that are removed by the blade removal tool based on the number of times a circuit formed by contacts on the blade removal tool being closed.

At 1502, a user inserts a blade to be removed onto the blade removal tool which includes contacts on either side. The blade spans a gap between the contacts on either side of the tool, and thus closes the circuit formed by the contacts at 1506. The microcontroller flags that the circuit has been closed at 1508. Then the user pulls the scalpel back, and removes the blade at 1510. The microcontroller detects that the circuit is open, and increments the count of removed blades at 1512. Another blade can be inserted onto the blade removal tool to be removed, and the microcontroller keeps counting the times of the circuit on the tool being closed.

After all blades are removed using the blade removal tool, the microcontroller provides, through an RFID transponder or tag, information related to the count of the removed blades along with additional information to an RFID receiver upon request at 1514. The RFID receiver identifies the received information and displays a final count of the removed blades on a system display at 1516. The user can read the final count of the removed blades on the system display at 1504. Optionally, the RFID receiver may transmit the received information to a central server for recording at 1516.

These flow charts are not intended to be the sole methods of operation. Rather, the flow charts are intended to illustrate the variety of methods than can be performed using the disclosed sharps containers.

It is known in the art to tag the outer packaging of items, including surgical items, with RFID transponders for the purpose of inventory control. In this document, the RFID reader 58 (see FIG. 4) and computer system 62 could be configured to detect each needle package via an RFID tag placed on the packaging material. This would establish an "in count" that would accurately represent the number of needles used in the surgical procedure. The reader and computer system could then compare this "in count" to the number of needles contained in the sharps container 10 (the "out count") via the methods and apparatus described herein. That would reduce the possibility for human error in the "in counting" process. The same is possible for scalpel blades.

Furthermore, the RFID tag associated with the needle or scalpel blade could be located inside the packaging of the needle or scalpel blade. The packaging of the suture or needle is often of the foil peel-pouch type and thus can be used to shield or detune an RFID transponder. The RFID transponder could be placed either removably or irremovably inside the foil packaging such that the tag cannot be read until the packaging is opened, or until the packaging is opened and the RFID transponder is removed from the packaging. This would establish an "in count" that would accurately represent the number of needles used in the surgical procedure. The reader and computer system could then compare this to the number of needles contained in the sharps container via the methods and apparatus described herein. This would further reduce the possibility for human error in the "in counting" process, because only needles in packages that were opened could be counted in.

While the present invention has been particularly shown and described with reference to the preferred embodiments thereof, it will be understood by those skilled in the art that various changes in form and detail may be made therein without departing from the spirit and scope of the invention. The following claims are intended to cover such changes in form and detail.

What is claimed is:

1. A sharps container having a magnetic material and at least one pair of contacts, and circuitry for determining the condition, open or closed, of said pair of contacts.

2. The container of claim 1, wherein a sharp being placed between the at least one pair of contacts closes a circuit.

3. The container of claim 1, additionally comprising means for generating an in count.

4. The container of claim 2, additionally comprising means for comparing the in count with the count of closed circuits.

5. The container of claim 1, wherein the circuitry includes a microcontroller.

6. The container of claim 1, wherein the circuitry communicates data related to the condition of the circuits formed by the at least one pair of contacts to an RFID receiver.

7. The container of claim 3, wherein the in count is generated through a manual input using a button or switch.

* * * * *